United States Patent [19]

Branner-Jørgensen

[11] 4,266,029

[45] May 5, 1981

[54] ENZYME IMMOBILIZATION

[75] Inventor: Sven Branner-Jørgensen, Charlottenlund, Denmark

[73] Assignee: Novo Industri A/S, Denmark

[21] Appl. No.: 65,532

[22] Filed: Aug. 10, 1979

[30] Foreign Application Priority Data

Aug. 14, 1978 [GB] United Kingdom ............... 33295/78

[51] Int. Cl.³ ............................................... C12N 11/14
[52] U.S. Cl. ................................... 435/176; 435/174; 435/177
[58] Field of Search ............... 435/174, 177, 180, 181, 435/182, 94, 176

[56] References Cited

U.S. PATENT DOCUMENTS

| | | | |
|---|---|---|---|
| 3,796,634 | 3/1974 | Haynes et al. | 435/180 |
| 3,838,007 | 9/1974 | Van Velzen | 435/181 |
| 3,928,143 | 12/1975 | Coughlin | 435/94 X |
| 3,980,521 | 9/1976 | Amotz et al. | 435/174 |
| 4,004,979 | 1/1977 | Arrameas et al. | 435/181 X |
| 4,138,290 | 2/1979 | McMullen et al. | 435/94 |
| 4,141,857 | 2/1979 | Levy et al. | 435/180 X |

OTHER PUBLICATIONS

Grittith, et al., A New Method for Coating Fermentation Tomer Packing So as to Facilitate Microorganism Attachment, Developments in Industrial Microbiology, vol. 17, 1976 (pp. 241-246).

Leroy et al., Insoluble Particles with Enzymic Activity, Chemical Abstracts, vol. 88: 59763w, 1978 (p. 164).

Hartmeier et al., Carrier-Fixed Enzymes Chemical Abstracts, vol. 88: 117655e, 1978 (p. 207).

Miyairi et al., Immobilization of Enzyme by Azide Compound, Chemical Abstracts, vol. 89: 19233n, 1978 (p. 257).

*Primary Examiner*—David M. Naff
*Attorney, Agent, or Firm*—Fidelman, Wolffe & Waldron

[57] ABSTRACT

An immobilized enzyme granular product suitable for use in expanded and fluidized bed operations is formed by gelatine coating a dense particulate material, e.g., a mineral oxide, and hardening the coating with glutaraldehyde, then treating the coated particles with a pasty mixture of an enzyme substance and polyethylene imine, and thereafter treating the mixture with glutaraldehyde, followed by granulating and drying. Sand and titanium dioxide are preferred particulate materials. Lactase, urease, and inulinase are preferred enzymes, preferably in the form of whole or homogenized microbial cells.

21 Claims, No Drawings

ENZYME IMMOBILIZATION

DESCRIPTION OF THE INVENTION

This invention relates to an immobilized enzyme product suited for use in an expanded or fluidized bed and to the process for production of such enzyme product.

BACKGROUND OF THE INVENTION

Use of immobilized enzymes in an expanded or fluidized bed has certain advantages over use of immobilized enzymes in a fixed bed. Reference is made to U.S. Pat. Nos. 3,928,143 and 4,138,290 for detailed discussion of how fluidized and expanded beds may be employed to carry out enzyme catalyzed reactions. The most important advantages of operating in an expanded or fluidized bed over the operating performance in a fixed bed is that plugging is totally avoided in an expanded or fluidized bed and that it is possible to use substrates with particulate materials therein in an expanded or fluidized bed.

In spite of these advantages, almost all industrially enzyme catalyzed continuous processes in which immobilized enzymes are used, to the date hereof, are performed in fixed bed, inter alia because in an expanded or fluidized bed the particles with the enzymatic activity are worn down during operation as a result of collisions between the individual particles.

Thus, a need exists for immobilized enzyme-containing particles suitable for use in an expanded or fluidized bed which have a better abrasion resistance than the previously known immobilized enzyme-containing particles that were purported to be suitable for use in an expanded or fluidized bed.

BRIEF DESCRIPTION OF THE INVENTION

The invention relates to a process for preparation of an immobilized enzyme product, which process comprises first coating a particulate, dense material with gelatine, treating the thus coated, dense material with glutaraldehyde. Separately a pasty mixture of an enzyme product and an aqueous polyethylene imine solution is prepared. The gelatine-coated and glutaraldehyde-treated particulate material is admixed with the paste to form a (still) pasty mixture. Then the thus formed pasty mixture is treated with glutaraldehyde to generate a more solid mass; whereafter the mass is granulated and dried.

Surprisingly coating of the particulate, dense material with gelatine and the treatment of the thus coated, particulate, dense material with glutaraldehyde in combination with the use of polyethylene imine on the enzyme and the later treatment of the pasty mixture with glutaraldehyde, provides an immobilized enzyme product wherein the enzymes adhere extremely strongly to the particulate dense material and the ultimate granules exhibit an exceptionally high abrasion resistance.

The invention also relates to the granular immobilized enzyme products of the process, including notably so immobilized urease, inulinase and lactase.

DETAILED DESCRIPTION OF THE INVENTION

In carrying out the process of this invention coating with gelatine is usually commenced by soaking gelatine in water, then discarding excess water, and thereafter melting the gelatine. The thus melted gelatine is mixed with 100 parts by wt of the particulate, dense material, forming a pasty mass of material. This pasty mass of material is treated with up to about 1 part by wt of glutaraldehyde, whereby the gelatine is hardened and the mass converts into a multiplicity of coated particles.

The paste of enzyme and polyethylene imine solution is formed by simply mixing around 20 parts of the enzyme product and around 2 parts of a polyethylene imine in solution. When this paste is then mixed with the gelatine-coated, glutaraldehyde-hardened particulate, dense material, another paste is formed, i.e., the mixture is still pasty, but after treatment with about 2 parts of glutaraldehyde the paste falls apart into granules. However, each granule contains therein two or more of the particles of dense material. The individual particles of dense material in each granule seem to be bonded together by the reaction product of the polyethylene imine and glutaraldehyde.

The final immobilized enzyme (granular) product thus consists of a multi-part granule in which the strength and abrasion resistance of the granule derive from the dense particles which form the outer borderlines of the granule, and in which the enzyme activity therein derive from the cross-linked mass of enzyme-containing material between and around the dense particles. The enzymatic activity is protected by the particulate dense material acting as a shield for the (less abrasion resistant) mass of enzyme-containing material.

As can be appreciated from the function of the dense material as a weighting and abrasion resistant support substance, the chemistry of the dense material forms no part of this invention, other than, of course, the desirability of its being water insoluble and inert. Thus, the metallic particles suggested in U.S. Pat. No. 3,928,143 may be employed. In addition, mineral oxides are suitable for practice of this invention, including notably, sand and titanium dioxide.

In a preferred embodiment of the invention the particulate dense material is sand, a cheap relatively dense material.

In another preferred embodiment of the invention the particulate dense material has a particle size of between 0.1 and 1 mm, a particle size interval appropriate for most expanded bed or fluidized bed operations.

In another preferred embodiment of the invention the particulate, dense material has a specific gravity exceeding 4 g/cm$^3$. By using particulate, dense material of more than 4 g/cm$^3$ expanded or fluidized bed enzymatic process can be controlled better, and liquids with relatively high specific gravity can be processed without difficulty. The particulate, dense material should be related to the specific gravity of the solution or mixture treated. The higher the specific gravity of the liquid to be processed in the expanded or fluidized bed, the higher should be the specific gravity of the dense material. Titanium dioxide is dense, highly inert and readily available; it is a preferred dense material for practice of this invention.

In another preferred embodiment of the invention the weight of the gelatine for the gelatine-coated particulate, dense material amounts to between 0.2% and 5% of the weight of the particulate, dense material, preferably between 0.5% and 2% thereof. This proportion of gelatine is optimal in relation to attainment of strong adhesion of the enzyme to the particles of the dense material.

In another preferred embodiment of the invention the weight of the glutaraldehyde with which the gelatine-coated particulate dense material is treated amounts to between 2% and 25% of the weight of the gelatine, preferably between 10% and 20% of the weight of the gelatine. This amount of glutaraldehyde is optimal in relation to attainment of strong adhesion of the enzyme to the particles of the particulate, dense material.

In another preferred embodiment of the invention the enzyme is urease. Providing an immobilized urease product allows a urea-containing liquid waste to be decomposed before being sent to the sewer, whereby environmental pollution requirements can be met in a simple and cheap manner.

Desirably the urease is prepared microbiologically from *Bacillus pasteurii*. This urease is well suited for the urea decomposition purpose; it has a good temperature stability and high activity at the pH levels of urea-containing waste.

Another preferred enzyme is lactase. Immobilization of lactase according to practice of this invention makes feasible a continuous conversion of the lactose in whey to glucose and galactose by an expanded or fluidized bed operation.

Another preferred enzyme is inulinase. Immobilization of inulinase according to practice of this invention makes it possible to convert inulin to fructose by an expanded or fluidized bed operation.

In another preferred embodiment of the invention the enzyme product consists of dried enzyme containing whole bacterial cells. The cells isolated from the enzyme fermentation broth in which the microorganism is cultivated may be left with the concomitants and fillers which are normal constituents of industrial enzyme products. Cultivation of the microorganism and recovery of a crude cell product as the ultimate product is a very cheap production method, as no treatment of the bacterial cells is necessary.

In another preferred embodiment of the invention the enzyme product consists of the crude whole bacterial cell product after subjecting the cells to partial or total homogenization. The product still contains the concomitants and fillers which are normal constituents of industrial enzyme products. Such a product has the advantage that it may be employed in substitution for a more expensive, more purified enzyme. Reference is made to U.S. Pat. No. 3,980,521 for more detailed discussion of recovery and homogenization methods applicable to intracellular enzymes such as urease, inulinase, lactase as well as the glucose isomerase to which that patent is directed.

Desirably the enzyme product, whether whole cells or homogenized cells, is spray dried after recovery from the broth and homogenization. It is simple and convenient to use a dry enzyme product for practice of this invention and a spray dried product is well suited for the process according to the invention.

In another preferred embodiment of the invention the weight of the polyethylene imine amounts to between 2 and 50% of the enzyme substance, i.e., cells and impurities, preferably between 5 and 15% of the enzyme product weight. Less polyethylene imine than 2% of the enzyme substance will not form an immobilized product with sufficient coherence, and more polyethylene imine than 50% of the enzyme substance will not produce any beneficial effect.

Desirably the polyethylene imine has a molecular weight between 300 and 100,000. These polyethylene imines are able to form an immobilized product with the best coherence.

In another preferred embodiment of the invention the weight of the glutaraldehyde, with which the pasty mixture of the imine treated enzyme and coated dense particles is treated, is between 10% and 1000% of the weight of the polyethylene imine, preferably between 50% and 200% of the weight of the polyethylene imine. Less glutaraldehyde than 10% of the weight of the polyethylene imine will not form a granule product with sufficient abrasion resistance, and more glutaraldehyde than 1000% of the weight of the polyethylene imine will not have any beneficial effect.

Drying of the granule product may be carried out as a fluid bed drying. This is cheap, effective and fully satisfactory, particularly since the abrasion resistance characteristic of the granules reduces drying losses.

The invention in its second aspect comprises a weighted immobilized enzyme granular product suited for enzymatic treatment of a liquid substrate in an expanded bed reactor. Such products are produced by the process of this invention.

In a preferred embodiment of the invention the weighted immobilized enzyme granular product is a weighted urease product suited for decomposition of urea in aqueous phase in an expanded bed reactor. This urease product can be produced as mentioned above and has utility for decomposition of urea solutions before they are transported to the sewer. Other preferred granular weighted enzyme products are lactase and inulinase.

For further understanding of this invention the following examples of practice thereof are provided.

EXAMPLE 1

1.8 g of gelatine was soaked in demineralized water for 10–15 minutes, the excess of water was discarded, and the gelatine was melted in a water bath.

180 g of beach sand was heated to 60° C. on a water bath.

Then the beach sand was poured into the gelatine with stirring in order to form a homogenous paste. The gelatine-treated sand was divided in two parts and treated with 0.2 and 0.1% glutaraldehyde, respectively (20% and 10% in relation to the amount of gelatine).

After the addition of glutaraldehyde, the mixture was agitated until the mass gelled and a particulate material with particles of homogenous size was formed, the time of gelation being around 1 minute.

2 g of spray dried urease with an activity of 6250 urease units/g and produced from *Bacillus pasteurii* NCIB 8841 was mixed with (1) 2 ml 5% PEI 600 (polyethylene imine with molecular weight 40,000–60,000, purchased from Dow Chemical Co.), (2) 2 ml 10% PEI 600 and (3) 3 ml 10% PEI 600 at pH 7; when a paste was formed 10 g of the above described gelatine treated beach sand was added, the mixing was then continued and thereafter immobilization was completed by adding 1.25, 1.75 or 2.25 ml of 25% glutaraldehyde with thorough mixing. The product was squeezed gently whereby it fell apart into a granulate.

The urease activity unit is measured in the following way. The analysis is performed in a pH-stat at pH 7.0 and 30° C. with 3% (0.5 M) urea in 0.2 M phosphate as a substrate. The reaction can be represented by the equation.

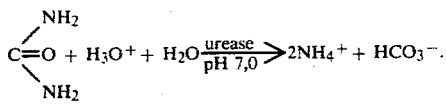

$$C(NH_2)(NH_2)=O + H_3O^+ + H_2O \xrightarrow[pH\ 7,0]{urease} 2NH_4^+ + HCO_3^-.$$

1 urease activity unit per definition splits 1 μmol of urease per minute under the above reaction conditions.

The table below indicates the conditions of immobilization and the activity of the formed granular products.

TABLE

| | Sand | | Immobilizing | | | Yield of dry product, g | Activity, batch pH 7 | | | |
|---|---|---|---|---|---|---|---|---|---|---|
| | | | Spray dried urease, g | 10% PEI 600, ml | 25% glutaraldehyde ml | | 300–700 μ | | 700–1000 μ | |
| Used Amount g | gelatine % | glutaraldehyde % | | | | | units/g | activity yield % | units/g | activity yield % |
| 1 | 10 | 1 | 0.1 | 2 | 2 | 1.75 | 11.5 | 287 | 26 | 336 | 31 |
| 2 | 10 | 1 | 0.2 | 2 | 2 | 1.75 | 11.5 | 276 | 25 | 326 | 30 |
| 3 | 10 | 1 | 0.1 | 2 | 1 + 1mlH₂O | 1.75 | 10.9 | 96 | 8.4 | 209 | 18 |
| 4 | 10 | 1 | 0.1 | 2 | 3 | 1.75 | 12.1 | 280 | 27 | 376 | 36 |
| 5 | 10 | 1 | 0.2 | 2 | 2 | 1.25 | 11.5 | 315 | 29 | 361 | 33 |
| 6 | 10 | 1 | 0.2 | 2 | 2 | 2.25 | 11.7 | 169 | 16 | 243 | 23 |

The physical strength of all the immobilized enzyme granular products were evaluated as good, no physical decomposition could be observed after 60 hours on a shaking table. A rougher manual treatment of the products indicated that products Nos. 3 and 5 were somewhat weaker than the other products. Product No. 6 is somewhat stronger than the others.

The products were tested as the active mass in a fluidized bed treatment of an aqueous solution containing 1% urea as a substrate. The urea was satisfactorily decomposed.

EXAMPLE 2

2 g lyophilized lactase with an activity of 973 lactase units/g and produced from Bacillus sp: NRRL B-11, 229 was mixed with 3 ml 10% PEI 15 T (polyethylene imine with molecular weight 700, purchased from Taihei Sangyo Kaisha Ltd.) at pH 7.0. When a paste was formed 10 g of gelatine treated sand, prepared as described in Example 1, was added. Mixing was continued, and the immobilization was completed by adding 1.75 ml of 25% glutaraldehyde. The product was squeezed gently whereby it fell apart as a granulate. After drying the activity was 25.5 lactase units/g and the activity yield was 16.3%.

Lactase activity is measured in the following way. The analysis is performed in a shaking water bath at 60° C. and pH 6.5 with 10% lactose in milk buffer as a substrate. The reaction is terminated by boiling for 10 minutes. The amount of glucose liberated in the supernatant is determined by means of the glucose oxidase peroxidase method (Tech. Bull. No. 510, Sigma Chemical Co.). 1 lactase activity unit per definition liberates 1 μmol of glucose per minute under the reaction conditions mentioned above.

No disintegration of the particles of immobilized lactase could be ascertained by visual inspection after continuous shaking in 20% lactose solution for one week.

EXAMPLE 3

2 g of spray dried inulinase with an activity of 105 inulinase units/g produced from *Kluyveromyces fragilis* (NRRL Y 1156), was mixed with 3 ml of neutralized 10% polyethylene-imine solution (PEI 15 T, Taihei Sangyo Kaisha Co., Ltd.). When a paste was formed 10 g of gelatine and glutaraldehyde treated sand, prepared as in Example 1 was added. The mixing process was continued, and the immobilization reaction completed by adding 1.75 ml of 25% solution of glutaraldehyde and mixing thoroughly. The product was squeezed gently, whereby it fell apart as a granulate, and air dried.

The activity of the product was 13.5 inulinase units/g corresponding to an activity yield of 77%.

The activity of the soluble enzyme was measured as μmol reducing sugar formed per minute at pH 4.7 and 50° C. with a 2.5% solution of inulin as a substrate.

The activity of the immobilized enzyme was measured as μmol reducing sugar formed per minute at pH 4.7 and 50° C. from a 5% solution of inulin as a substrate in a shaking bath.

I claim:

1. Process for preparation of an immobilized enzyme product which comprises:
    coating a particulate, dense material with gelatine then treating the so-coated material of particle size between about 0.1 and 1 mm with glutaraldehyde;
    preparing a paste comprising an enzyme product and an aqueous polyethylene imine solution;
    mixing the glutaraldehyde treated particulate material with the paste;
    thereafter treating the resulting pasty mixture with glutaraldehyde to form a mass; and
    granulating and drying the said mass.
2. The process of claim 1 wherein the particulate, dense material is sand.
3. The process of claim 1 wherein the particulate, dense material has a specific gravity exceeding 4 g/cm³.
4. The process of claim 1 wherein the particulate, dense material is titanium dioxide.
5. The process of claim 1 wherein the weight of the gelatine in the gelatine-coated particulate, dense material amounts to between 0.2 and 5% of the weight of the particulate, dense material.
6. The process of claim 5 wherein the weight of the gelatine in the gelatine-coated particulate, dense material amounts to between 0.5 and 2% of the weight of the particulate, dense material.
7. The process of claim 1 wherein the weight of the glutaraldehyde with which the gelatine-coated particulate, dense material is treated amounts to between 2 and 25% of the weight of the gelatine.
8. The process of claim 7 wherein the weight of the glutaraldehyde with which the gelatine-coated particulate, dense material is treated, amounts to between 10 and 20% of the weight of the gelatine.

9. The process of claim 1 wherein the enzyme is urease.

10. The process of claim 9 wherein the urease is from *Bacillus pasteurii*.

11. The process according to claim 1 wherein the enzyme is lactase.

12. The process of claim 1 wherein the enzyme is inulinase.

13. The process of claim 1 wherein the enzyme product comprises enzyme-containing whole bacterial cells.

14. The process according to claim 1 wherein the enzyme product comprises enzyme-containing bacterial cells which are at least partly homogenized.

15. The process of claim 1 wherein the weight of polyethylene imine amounts to between 2 to 50% of the enzyme product.

16. The process of claim 15 wherein the weight of polyethylene imine amounts to between 5 and 15% of the enzyme product.

17. The process according to claim 1 wherein the polyethylene imine has a molecular weight of between 300 and 100,000.

18. The process of claim 1 wherein the weight of glutaraldehyde with which the pasty mixture is treated amounts to between 10 and 1000% of the weight of the polyethylene imine.

19. The process of claim 18 wherein the weight of glutaraldehyde with which the pasty mixture is treated amounts to between 50% and 200% of the weight of the polyethylene imine.

20. An enzyme product, suited for decomposing a liquid substrate in an expanded bed reactor, which comprises the immobilized enzyme product prepared by the process of claim 1.

21. A urease product, suited for decomposing urea in an aqueous phase in an expanded bed reactor, which comprises the immobilized urease product prepared by the process of claim 9.

* * * * *